Figures 1, 2, 3:
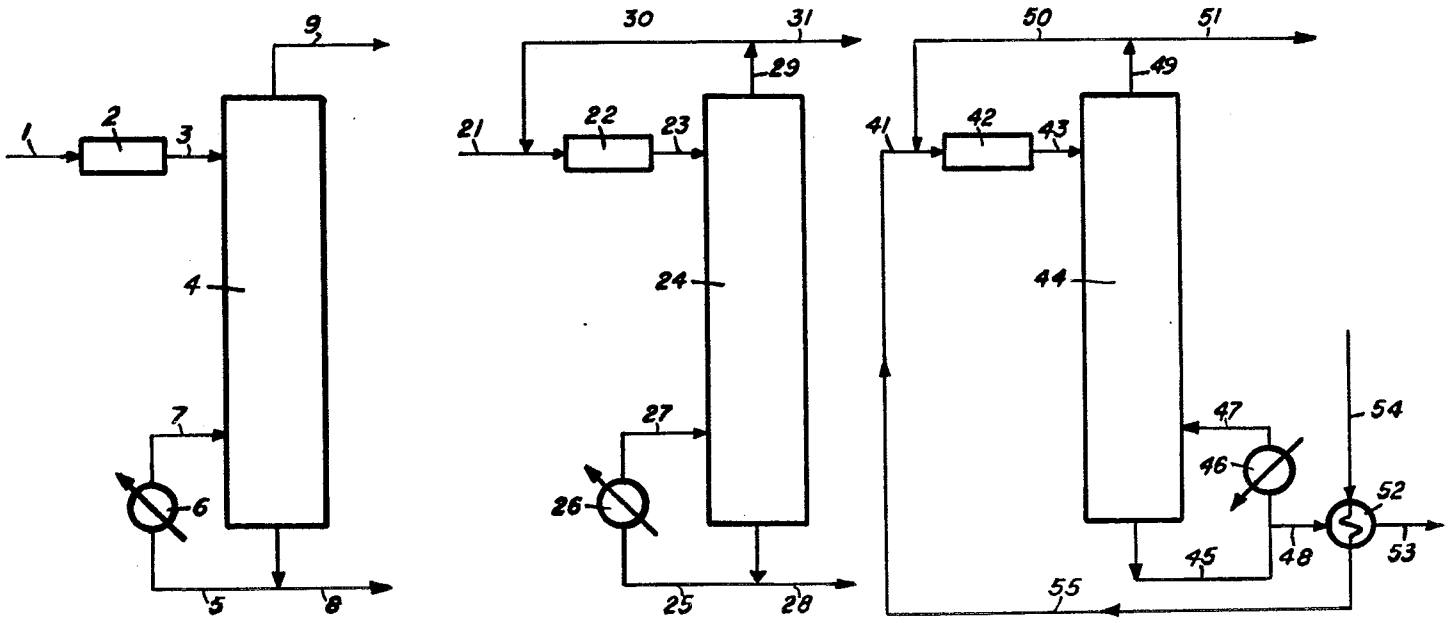
Figure 4:
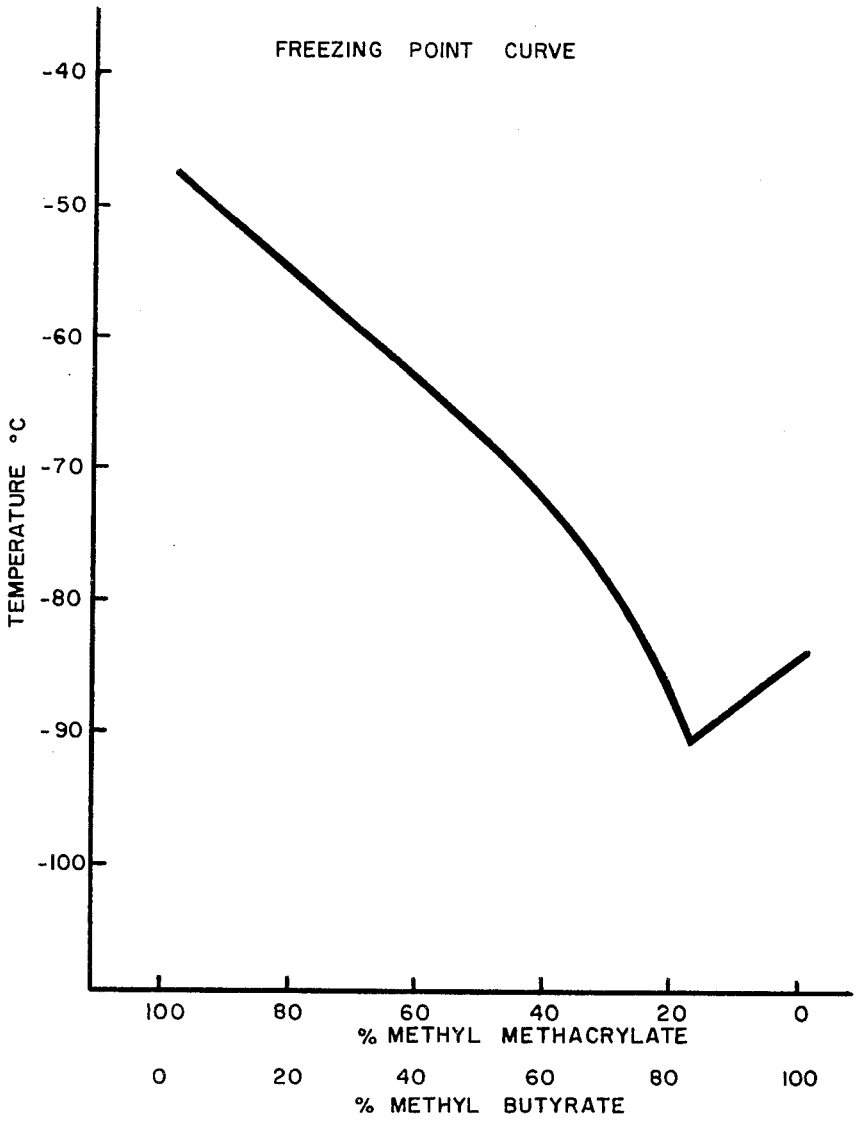

United States Defensive Publication [19] (H) [11] T955,005

Stutler et al. [43] Feb. 1, 1977

[54] PROCESS FOR PURIFICATION OF ALKYL METHACRYLATES

[76] Inventors: Athey C. Stutler; Max Statman; Alden E. Blood, all of P.O. Box 2068, Longview, Tex. 75601

[21] Appl. No.: 161,356

[22] Filed: July 9, 1971

Related U.S. Application Data

[63] Continuation of Ser. No. 693,392, Dec. 26, 1967, abandoned.

[51] Int. Cl. ..... C07c 69/54

[52] U.S. Cl. ..... 260/486 R

[57] ABSTRACT

Alkyl methacrylates are obtained free of impurities such as alkyl butyrates and assorted alkyl iodides by the partial crystallization of the crude alkyl methacrylate composition and subsequently contacting said crystals of alkyl methacrylate with liquid alkyl methacrylate to thereby free the crystals of occluded impurities.

15 Claims, 2 Sheets Drawing,

18 Pages Specification

The file of this unexamined application may be inspected and copies thereof may be purchased (849 O.G. 1221, Apr. 9, 1968).